July 22, 1947. G. DE RUITER Plant Pat. 745
ROSE PLANT
Filed Dec. 8, 1942
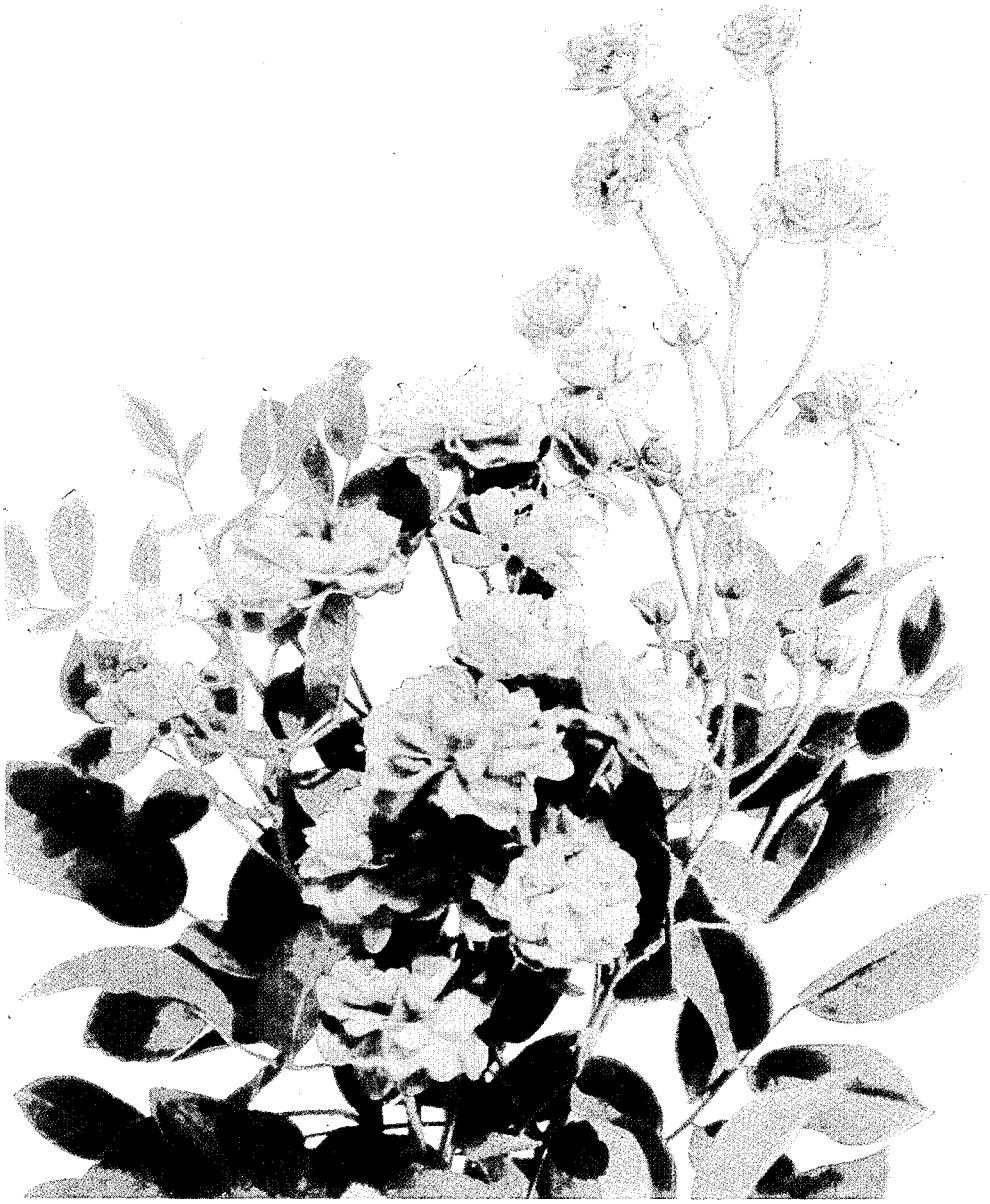
Inventor
G. de Ruiter
By Robert Robb
Attorney Patented July 22, 1947

Plant Pat. 745

UNITED STATES PATENT OFFICE

745

ROSE PLANT

Gerrit de Ruiter, Hazerswoude, Netherlands, assignor to Jackson & Perkins Company, Newark, N. Y., a corporation of New York Application December 8, 1942, Serial No. 468,294

1 Claim. (Cl. 47—61)

The present discovery relates to a new and distinct variety of rose plant, originating as a sport of the known "Gloire du Midi" (Plant Patent No. 270).

This new rose belongs to the class of polyanthas and its claim to distinctiveness lies particularly in the intense scarlet color and in the fully double, polyantha-sized flowers; that is to say, the individual flowers of the plant are fully double, having twice as many petals as that of "Gloire du Midi" bloom. This full doubleness makes it much longer lasting and a much better rose for pot forcing. It is also primarily distinguished from its parent in the absence of the orange suffusion which characterizes the flower of the said parent variety. Further the individual flowers retain their color in the group, completing a uniform cluster until they finally drop off.

Other primary distinctions of this new variety reside in its freedom of blooming and in the more or less commercial advantage of ease of handling in greenhouse forcing, inasmuch as this variety always gives a good crop of flowers when forced in pots in the greenhouse.

In still other detail respects, the new variety differs from known roses in its class, as more specifically set forth in the following description of the rose, in which the color terminology accords with Ridgway's Color Standard.

Asexual reproduction of this new variety shows the foregoing characteristics come true to form and are established.

Parentage: Sport.

*Parent variety.*—Sport of "Gloire du Midi."

Classification:

*Botanic and commercial.*—Polyantha.

*Flower*

(Observations made in the greenhouse of Jackson & Perkins Company, Newark, New York.)

Blooming habit: Recurrent—continuous.

Bud:

*Size.*—Small.

*Form.*—Short with flat top. Is not affected by wet or hot weather.

*Color.*—When sepals first divide—Rose Doree, Plate 1. When petals begin to unfurl—Scarlet Red, Plate 1. When half blown—inside of petals, Scarlet Red, Plate 1; reverse of petals, between Scarlet Red, Plate 1, and Rose Doree, Plate 1.

*Sepals.*—Slightly serrated. Curl back when petals unfurl. Color—upper side, Oil Green, Plate 5, edged with Yellowish Glaucous, Plate 41; under side, Lettuce Green, Plate 5, edged with Yellowish Glaucous, Plate 41.

*Calyx.*—Shape—funnel. Size—small. Aspect—smooth. Color—Absinthe Green, Plate 31.

*Peduncle.*—Length—long. Aspect—prickly. Color—Absinthe Green, Plate 31. Strength—Erect; slender.

*Opening.*—Bud opens well. Is not affected by adverse conditions.

Bloom:

*Size.*—Small. Average size when fully expanded, 1¼".

*Borne.*—In clusters, pyramidal.

*Stems.*—Medium length; strong.

*Form.*—When first open—flat. Permanence—retains its form to the end.

*Petalage.*—Very double (many petals and very few stamens hidden). Number of petals under normal conditions, 30.

*Color.*—Center of flower—between Scarlet, Plate I, and Peach Red, Plate 1. Outer petals—Scarlet, Plate I. Base of petals (aiglet)—Marguerite Yellow, Plate 30, and extends about one-third of the petal. Inside of petals—Scarlet, Plate I. Reverse of petals—between Scarlet, Plate I, and Peach Red, Plate 1. General tonality from a distance—Scarlet, Plate I.

*Discoloration.*—General tonality at end of first day—Scarlet, Plate 1. Second day—Scarlet, Plate 1. Third day—between Scarlet, Plate 1, and Peach Red, Plate 1.

Petals:

*Texture.*—Thin. Is not affected by wet or hot weather.

*Appearance.*—Inside—satiny. Outside—shiny.

*Form.*—Notched.

*Arrangement.*—Imbricated (regularly arranged shingle-like). Petaloids in center—none.

*Persistence.*—Drop off cleanly.

*Fragrance.*—None.

*Lasting quality.*—On the plant and as cut flower, long.

Genital organs:

*Stamens, anthers.*—Small; few. Color—Aniline Yellow, Plate 4. Arrangement—regular around styles.

*Stamens, filaments (threads).*—Short. Color—Naples Yellow, Plate 16.

*Pollen.*—Primuline Yellow, Plate 16.

*Styles.*—Columnar, uneven length; short; thin.

*Stigmas.*—Baryta Yellow, Plate 4.

*Ovaries.*—All enclosed in calyx.

*Plant*

Form: Bush.

Growth: Vigorous; compact.

Foliage: 5–7 leaflets.

*Size.*—Medium.

*Quantity.*—Normal.

*Color.* — New foliage — upper side, Calla Green, Plate 5; under side, Cress Green, Plate 31. Old foliage—upper side, Cress Green, Plate 31; under side, Light Cress Green, Plate 31.

*Shape.*—Oval.

*Texture.* — Upper side — smooth. Under side—rough. Ribs and veins—ordinary.

*Edge.*—Serrated (saw toothed).

*Serration.*—Single, small.

*Rachis.*—Light Cress Green, Plate 31. Under side—smooth.

*Stipules.*—Medium length; bearded.

*Disease resistance.*—Resistant.

Wood:

*New wood.*—Color—Lettuce Green, Plate 5. Bark—smooth.

*Old wood.*—Color—Cress Green, Plate 5. Bark—smooth.

Thorns (thorns are divided into thorns, prickles, and short needles):

*Thorns.*—Quantity—on main stalks from base and on laterals from stalk, few. Form—narrow base; short; hooked downward. Color when young—Chamois, Plate 30. Position—irregular.

*Prickles.*—On main stalks and on laterals—none.

*Short needles.*—On main stalks and on laterals—none.

I claim:

A new and distinct variety of rose plant, characterized as to novelty by the intense scarlet color in the fully double, polyantha-sized, flowers produced thereby, persistence of the color and uniformity in cluster groups until flowers drop off, the freedom of its blooming habit, and ease of handling in greenhouse forcing, substantially as shown and described.

GERRIT DE RUITER.